(12) United States Patent
Hoshika et al.

(10) Patent No.: US 9,970,396 B2
(45) Date of Patent: May 15, 2018

(54) INTAKE AIR HUMIDITY MEASUREMENT DEVICE FOR AN INTERNAL COMBUSTION ENGINE

(71) Applicant: Hitachi Automotive Systems, Ltd., Hitachinaka-shi, Ibaraki (JP)

(72) Inventors: Hiroaki Hoshika, Hitachinaka (JP); Takayuki Yogo, Hitachinaka (JP); Takahiro Miki, Hitachinaka (JP); Takeo Hosokawa, Hitachinaka (JP); Yuki Isoya, Hitachinaka (JP)

(73) Assignee: Hitachi Automotive Systems, Ltd., Hitachinaka-shi (JP)

( * ) Notice: Subject to any disclaimer, the term of this patent is extended or adjusted under 35 U.S.C. 154(b) by 93 days.

(21) Appl. No.: 15/102,404

(22) PCT Filed: Nov. 10, 2014

(86) PCT No.: PCT/JP2014/079661
§ 371 (c)(1),
(2) Date: Jun. 7, 2016

(87) PCT Pub. No.: WO2015/087644
PCT Pub. Date: Jun. 18, 2015

(65) Prior Publication Data
US 2017/0016415 A1 Jan. 19, 2017

(30) Foreign Application Priority Data
Dec. 10, 2013 (JP) .................... 2013-255332

(51) Int. Cl.
*G01M 15/05* (2006.01)
*F02M 35/10* (2006.01)
(Continued)

(52) U.S. Cl.
CPC .... *F02M 35/10393* (2013.01); *G01M 15/042* (2013.01); *G01N 27/223* (2013.01)

(58) Field of Classification Search
USPC ...................................... 73/114.31
See application file for complete search history.

(56) References Cited

U.S. PATENT DOCUMENTS

2002/0078733 A1  6/2002 Seakins et al.
2002/0116995 A1* 8/2002 Watanabe ............ G01F 1/6842
                                                    73/202.5
(Continued)

FOREIGN PATENT DOCUMENTS

EP   2 508 881 A1  10/2012
EP   3 128 318 A1   2/2017
(Continued)

OTHER PUBLICATIONS

International Search Report (PCT/ISA/210) issued in PCT Application No. PCT/JP2014/079661 dated Feb. 17, 2015 with English-language translation (four (4) pages).
(Continued)

*Primary Examiner* — Eric S McCall
(74) *Attorney, Agent, or Firm* — Crowell & Moring LLP

(57) ABSTRACT

A humidity measuring device includes an apparatus that determines whether or not a water droplet adheres to a surface of a sensor element which detects the humidity, based on changes in humidity and temperature of the intake air. The apparatus calculates a determination value based on a rate of change of the temperature and a rate of change of relative humidity. The apparatus also compares the determination value with a threshold. The apparatus also determines that a water droplet adheres to the surface of the
(Continued)

sensor element when a state where the determination value is larger than the threshold continues for a determination time or longer.

10 Claims, 11 Drawing Sheets

(51) Int. Cl.
  *G01N 27/22* (2006.01)
  *G01M 15/04* (2006.01)

(56) References Cited

U.S. PATENT DOCUMENTS

| | | | | |
|---|---|---|---|---|
| 2010/0031737 A1* | 2/2010 | Saito | ............ | G01F 1/6842 |
| | | | | 73/114.33 |
| 2012/0198925 A1* | 8/2012 | Saito | ............ | F02D 41/187 |
| | | | | 73/114.33 |
| 2014/0216146 A1* | 8/2014 | Yogo | ............ | G01F 1/684 |
| | | | | 73/114.31 |
| 2014/0283596 A1 | 9/2014 | Hosokawa et al. | | |
| 2014/0290359 A1* | 10/2014 | Saito | ............ | G01N 25/56 |
| | | | | 73/335.02 |
| 2017/0205261 A1* | 7/2017 | Yogo | ............ | G01F 1/684 |

FOREIGN PATENT DOCUMENTS

| | | |
|---|---|---|
| JP | 10-170465 A | 6/1998 |
| JP | 2003-75385 A | 3/2003 |
| JP | 2003-185614 A | 7/2003 |
| JP | 2005-31090 A | 2/2005 |
| JP | 2007-333750 A | 12/2007 |
| JP | 2009-92523 A | 4/2009 |
| JP | 2010-237128 A | 10/2010 |
| JP | 2010-237130 A | 10/2010 |
| JP | 2013-83453 A | 5/2013 |
| JP | 2013-96708 A | 5/2013 |
| WO | WO 2013/061740 A1 | 5/2013 |

OTHER PUBLICATIONS

Japanese-language Written Opinion (PCT/ISA/237) issued in PCT Application No. PCT/JP2014/079661 dated Feb. 17, 2015 (five (5) pages).
Extended European Search Report issued in counterpart European Application No. 14869543.0 dated Jun. 13, 2017 (Seven (7) pages).

* cited by examiner

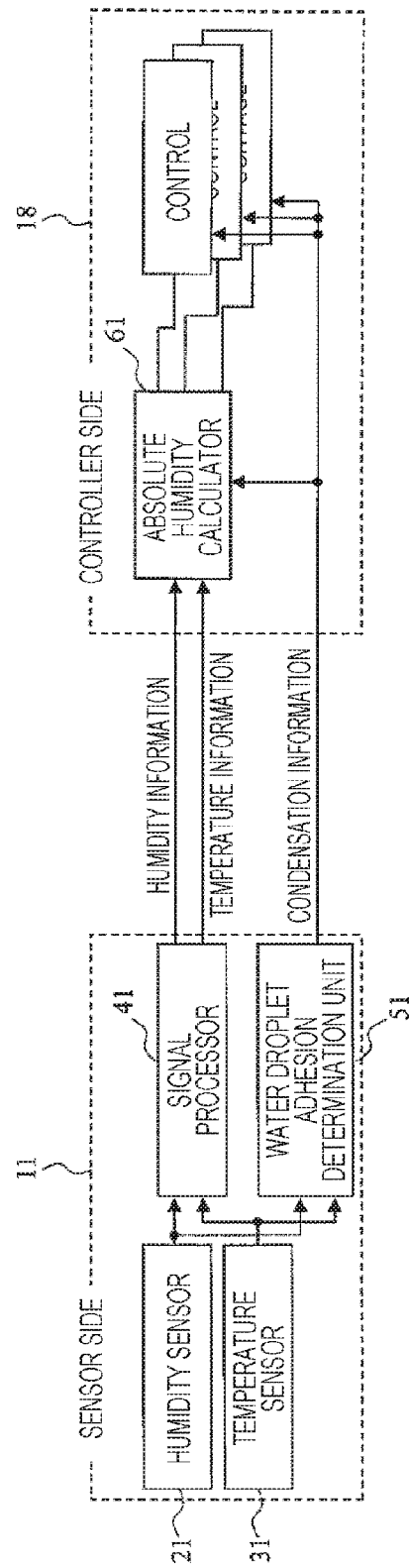

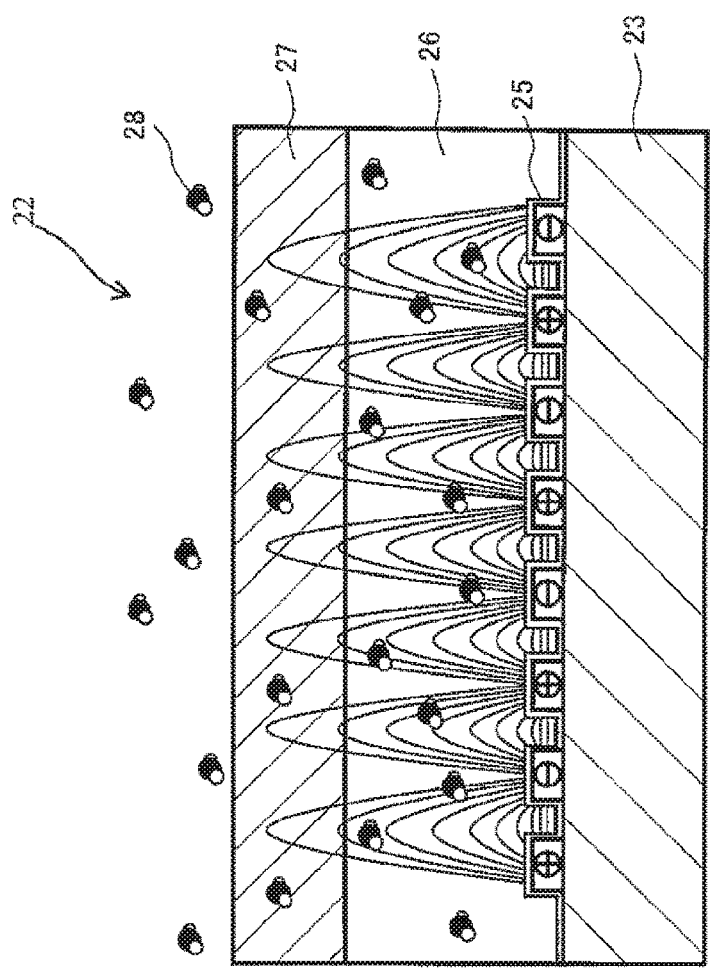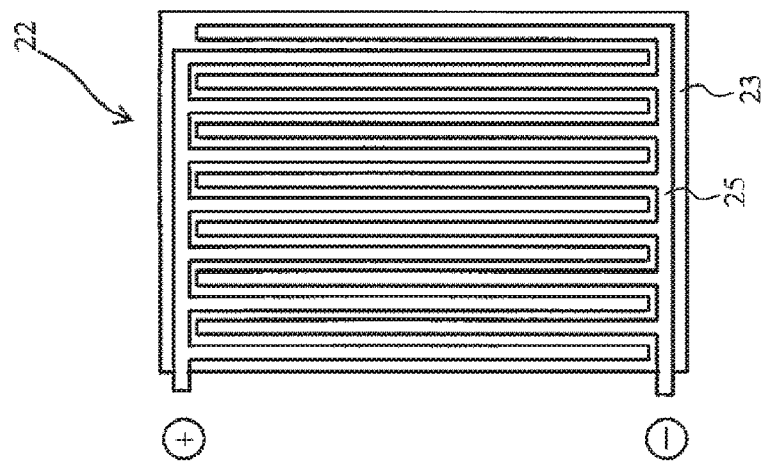

INTAKE AIR HUMIDITY MEASUREMENT DEVICE FOR AN INTERNAL COMBUSTION ENGINE

TECHNICAL FIELD

The present invention relates to a humidity measuring device for measuring humidity of the intake air taken into an internal-combustion engine of an automobile, for example.

BACKGROUND ART

When a water droplet adheres to a surface of a sensor element of a humidity sensor due to dew condensation or water splash, it is difficult to detect correct humidity of a gas. For example, PLT 1 describes that when dew condensation occurs on a surface of a sensor element of a humidity sensor, as an electrostatic capacitance value varies extremely, dew condensation on the surface of the sensor element can be detected by monitoring the variation thereof.

CITATION LIST

Patent Literature

PTL 1: Japanese Patent Application Laid-Open No. 2005-31090

SUMMARY OF INVENTION

Technical Problem

However, when a water droplet adheres to a surface of a sensor element, the humidity sensor indicates a humidity value of near 100%. As such, even though only the variation of the value is monitored, it is impossible to determine whether the value is given due to adhesion of a water droplet or the gas is actuary in a high humidity state. Further, once a water droplet covers the surface of a sensor element, gas humidity cannot be detected until the water droplet is removed. As such, it is impossible to know when a detection value by the humidity sensor is valid and when it is invalid.

The present invention has been made in view of the above problem. An object of the present invention is to provide a humidity measuring device capable of determining whether or not a detection value by a humidity sensor is valid.

Solution to Problem

A humidity measuring device according to the present invention to solve the above issue is a humidity measuring device for measuring humidity of intake air in an internal-combustion engine, including a water droplet adhesion determination unit for determining whether or not a water droplet adheres to a surface of a sensor element which detects the humidity, based on changes in humidity and temperature of the intake air.

Advantageous Effects of Invention

According to the invention, it is possible to accurately determine whether or not a humidity measurement value is valid. It should be noted that problems, configurations, and effects other than those described above will become apparent from the description of the embodiments provided below.

BRIEF DESCRIPTION OF DRAWINGS

FIG. 2 is a function block diagram illustrating an embodiment of a humidity measuring device according to the present invention FIGS. 3A and 3B illustrate an exemplary configuration of a relative humidity sensor.

DESCRIPTION OF EMBODIMENTS

Next, embodiments of the present invention will be described below with use of the drawings.

First Embodiment

Figure 1:
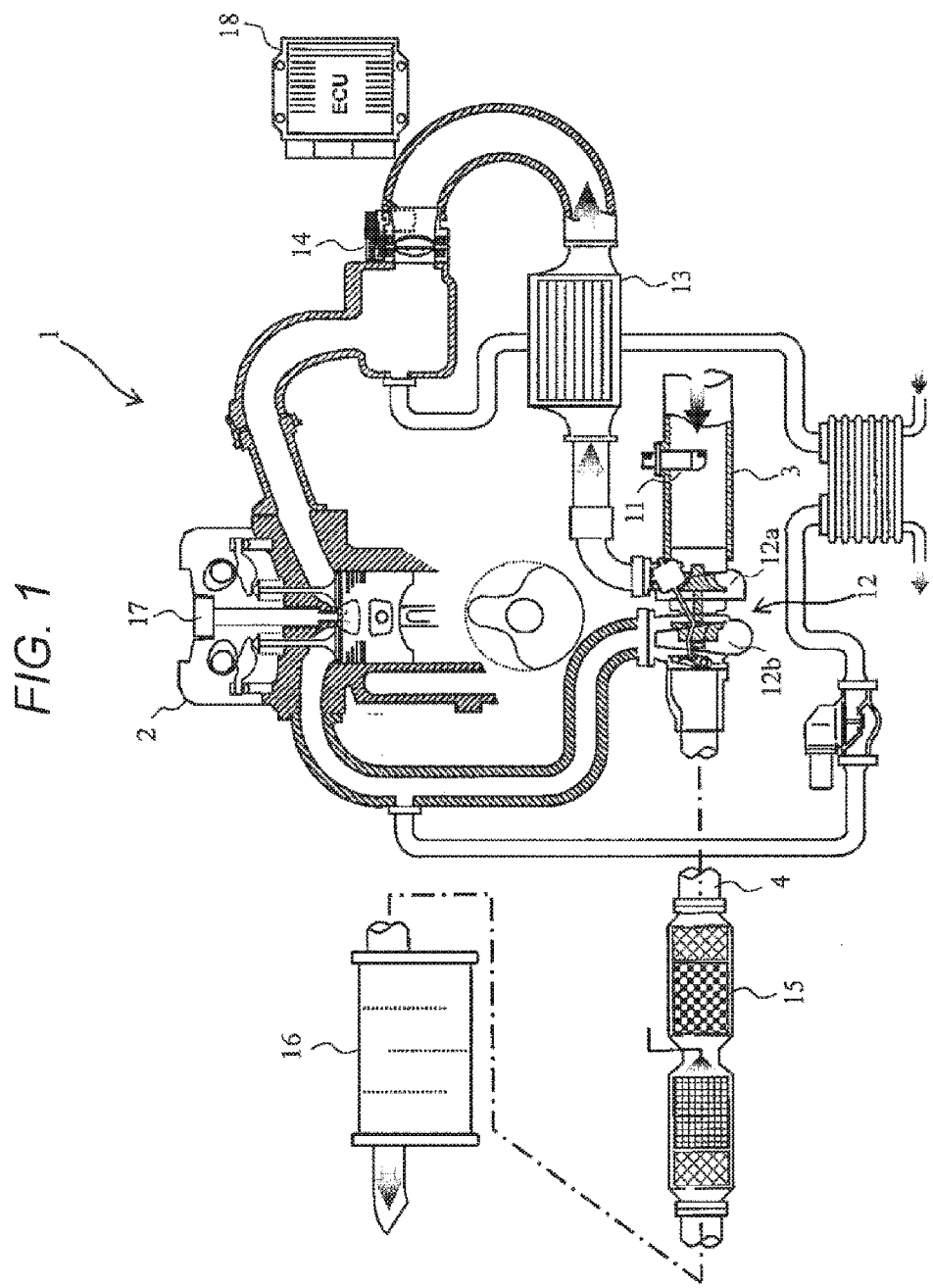
FIG. 1 is a schematic diagram of an engine control system to which a humidity measuring device of the present embodiment is applied.

FIG. 1 is a schematic diagram of an engine control system to which a humidity measuring device of the present embodiment is applied. FIG. 2 is a function block diagram illustrating an embodiment of a humidity measuring device according to the present invention.

A humidity measuring device is incorporated in an engine control system 1 of an automobile. As shown in FIG. 1, the engine control system 1 includes an engine body 2 which is an internal-combustion engine, an air intake passage 3 for supplying intake air to the engine body 2, and an exhaust passage 4 for discharging exhaust gas from the engine body 2. In the air intake passage 3, a compressor 12a of a turbocharger 12 is interposed at an intermediate position thereof, and an air flow sensor 11 is arranged at a position upstream of the compressor 12a. Further, an intercooler 13, an electronically-controllable throttle valve 14, a supercharging pressure sensor, and the like are arranged at positions downstream of the compressor 12a.

In the exhaust passage 4, a turbine 12b of the turbocharger 12 is interposed at an intermediate position thereof, and a catalyst 15 and a muffler 16 are arranged at positions downstream of the turbine 12b. The engine body 2 is provided with a high-pressure fuel injector 17 which injects fuel into the combustion chamber, and an ignition plug not shown. The engine body 2 is also provided with a crank angle sensor which detects an engine speed, a water temperature sensor which detects the temperature of cooling water in the engine body, and the like.

The air flow sensor 11 includes a flow rate sensor which detects a flow rate of the intake air, and also includes a humidity sensor 21 for detecting the humidity of the intake air, and a temperature sensor 31 (see FIG. 2) for detecting the temperature of the intake air. This means that in the present embodiment, the humidity sensor 21 and the temperature sensor 31 are provided to the air flow sensor 11.

Respective sensor signals of the air flow sensor 11, the crank angle sensor, the water temperature sensor, and the like are input to an ECU 18 which is a control computer of the engine control system 1, and are used for engine operation control such as ignition timing control and fuel injection control.

As shown in FIG. 2, the air flow sensor 11 includes a signal processor 41 and a water droplet adhesion determination unit 51. The signal processor 41 processes a signal of the humidity sensor 21 and a signal of the temperature sensor 31 to generate humidity information and temperature information, and performs processing to output them to the ECU 18. The water droplet adhesion determination unit 51 determines whether or not a water droplet adheres to the surface of the sensor element of the humidity sensor 21, based on the respective output signals of the humidity sensor 21 and the temperature sensor 31, and outputs a determination result to the ECU 18. The ECU 18 has an absolute humidity calculator 61 which calculates absolute humidity based on the humidity information and the temperature information. The absolute humidity, calculated by the absolute humidity calculator 61, and the determination result are used in various types of engine operation control performed by the ECU 18.

Figure 9:
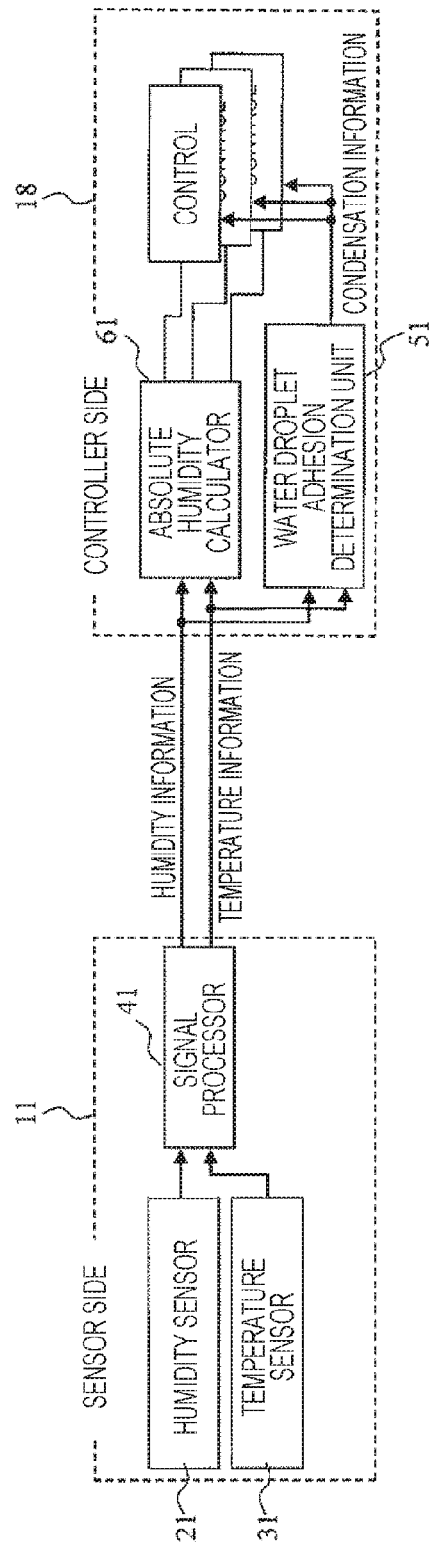
FIG. 9 is a function block diagram illustrating an exemplary variation of a humidity measuring device according to the present invention

In the present embodiment, the humidity measuring device of the present invention is configured of the relative humidity sensor 21, the temperature sensor 31, the signal processor 41, and the water droplet adhesion determination unit 51, of the air flow sensor 11, and the absolute humidity calculator 61 of the ECU 18. It should be noted that as shown in FIG. 9, the water droplet adhesion determination unit 51 may be provided to the ECU 18, rather than the air flow sensor 11.

Figure 4:
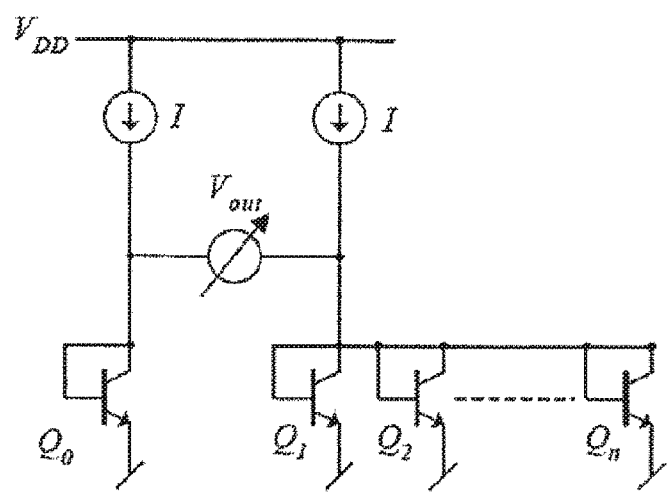
FIG. 4 illustrates an exemplary configuration of a temperature sensor.

FIGS. 3(a) and 3(b) show an exemplary configuration of the relative humidity sensor, in which FIG. 3(a) is a front view of the relative humidity sensor, and FIG. 3(b) shows a cross-section view thereof. FIG. 4 shows an exemplary configuration of the temperature sensor. As the relative humidity sensor 21 and the temperature sensor 31, publicly known ones may be used.

The humidity sensor 21 is a relative humidity sensor of an electrostatic capacitance type, and has a sensor element 22 which detects humidity. As shown in FIG. 3(a) and FIG. 3(b) the sensor element 22 has a structure that a comb-shaped electrode pair 25 and 25 is provided on the upper surface of a silicon substrate 23, which is covered with a hygroscopic high-molecular polymer film 26. The electrostatic capacitance of the electrode pair 25 and 25 varies according to moisture absorption by the high-molecular r polymer film 26. The variation of the electrostatic capacitance has a high correlation with relative humidity, so that it is possible to detect relative humidity by measuring the electrostatic capacitance. Electrode structure includes a plurality of types, such as one in which polymer is interposed between the top and bottom electrodes. The high-molecular polymer film 26 has a protective film 27 provided on the upper surface thereof. The intake air passes the outside of the protective film 27, and water molecules 28 are absorbed by the high-molecular polymer film 26. The surface of the protective film 27 forms the surface of the sensor element 22 of the humidity sensor 21, to which a water droplet may adhere due to a water splash included in the intake air or dew condensation.

The temperature sensor 31 is provided near the humidity sensor 21 in order to measure the temperature near the humidity sensor 21. As the temperature sensor 31, a semiconductor temperature sensor of a band-gap type may be used, for example, an exemplary circuit configuration of which is shown in FIG. 4.

Next, determination processing performed by the water droplet adhesion determination unit 51 will be described in detail. The water droplet adhesion determination unit 51 determines whether or not a water droplet adheres to the surface of the sensor element 22, based on changes in the humidity and the temperature of the intake air. In the present embodiment, it is determined that a water droplet adheres to the surface of the sensor element 22 when the condition shown by the following Expression (1) is continued for a predetermined determination time or longer.

[Expression 1]

$$Th_{Id} < Id = \frac{\Delta T}{\Delta RH} \tag{1}$$

Here, $\Delta T$ represents a rate of change of the temperature, $\Delta RH$ represents a rate of change of the relative humidity, Id represents an index which is a determination value calculated based on the rate of change $\Delta T$ of the temperature and the rate of change $\Delta RH$ of the relative humidity, and $Th_{Id}$ represents a threshold.

As shown by Expression (1), the water droplet adhesion determination unit 51 calculates the index Id based on the rate of change $\Delta T$ of the temperature and the rate of change of the relative humidity $\Delta RH$, compares the index Id with the threshold $Th_{Id}$, and determines whether or not the index Id is larger than the threshold ThId. Then, when a state where the index Id is larger than the threshold ThId continues for the determination time or longer, the water droplet adhesion determination unit 51 determines that a water droplet adheres to the surface of the sensor element 22.

Figure 5:
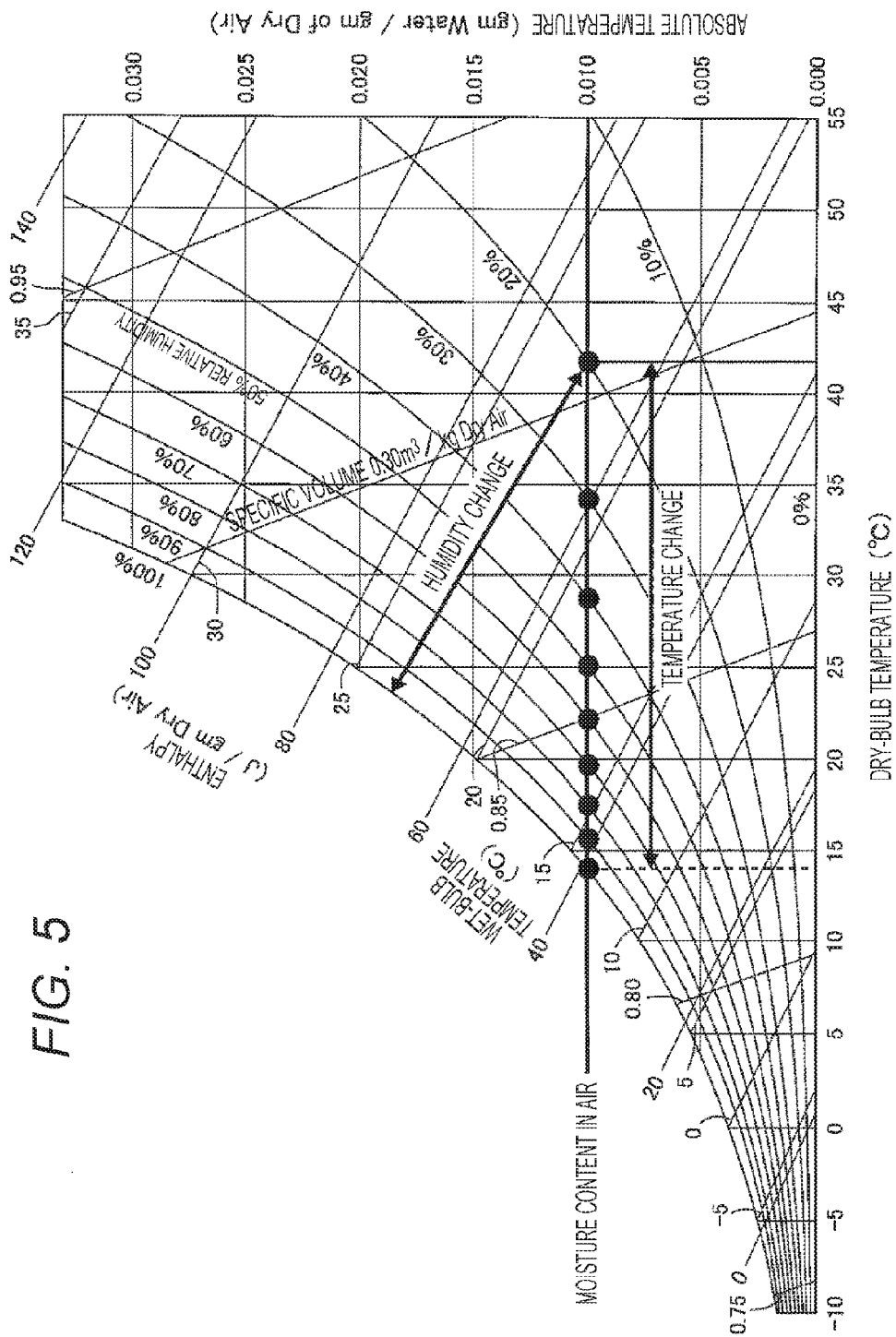
FIG. 5 is an air diagram showing a relationship among dry-bulb temperature, absolute humidity, and relative humidity of the intake air.
Figure 6:
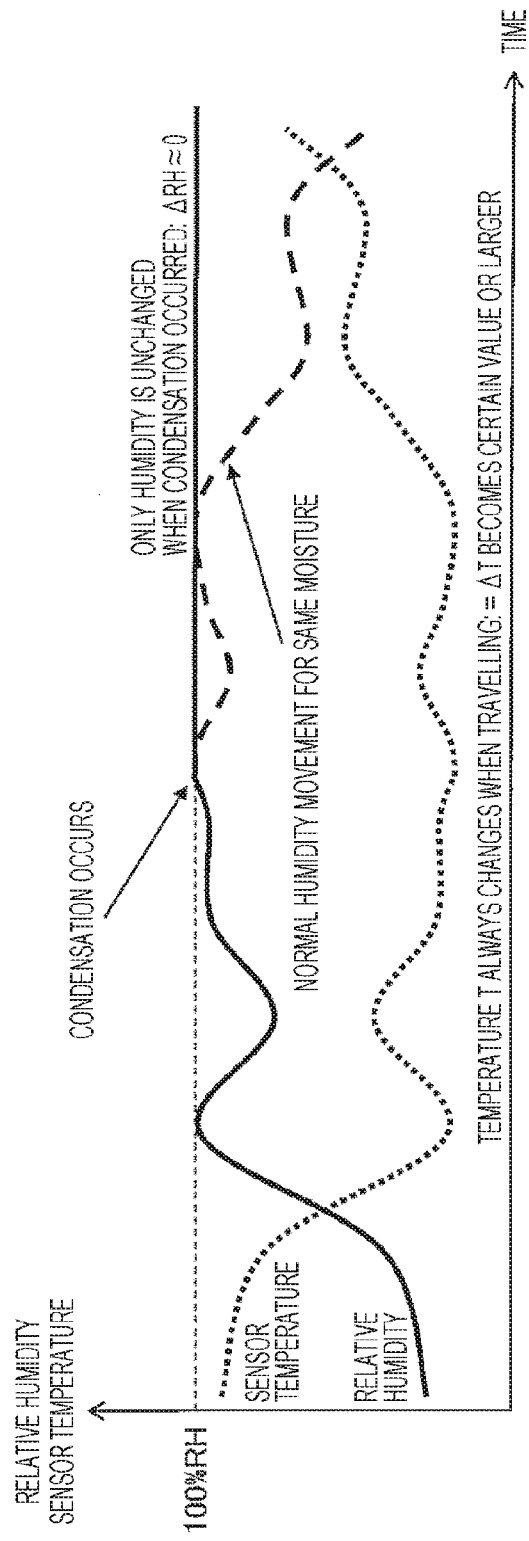
FIG. 6 is a graph showing a relationship between a change in relative humidity and a change in temperature.
Figure 7:
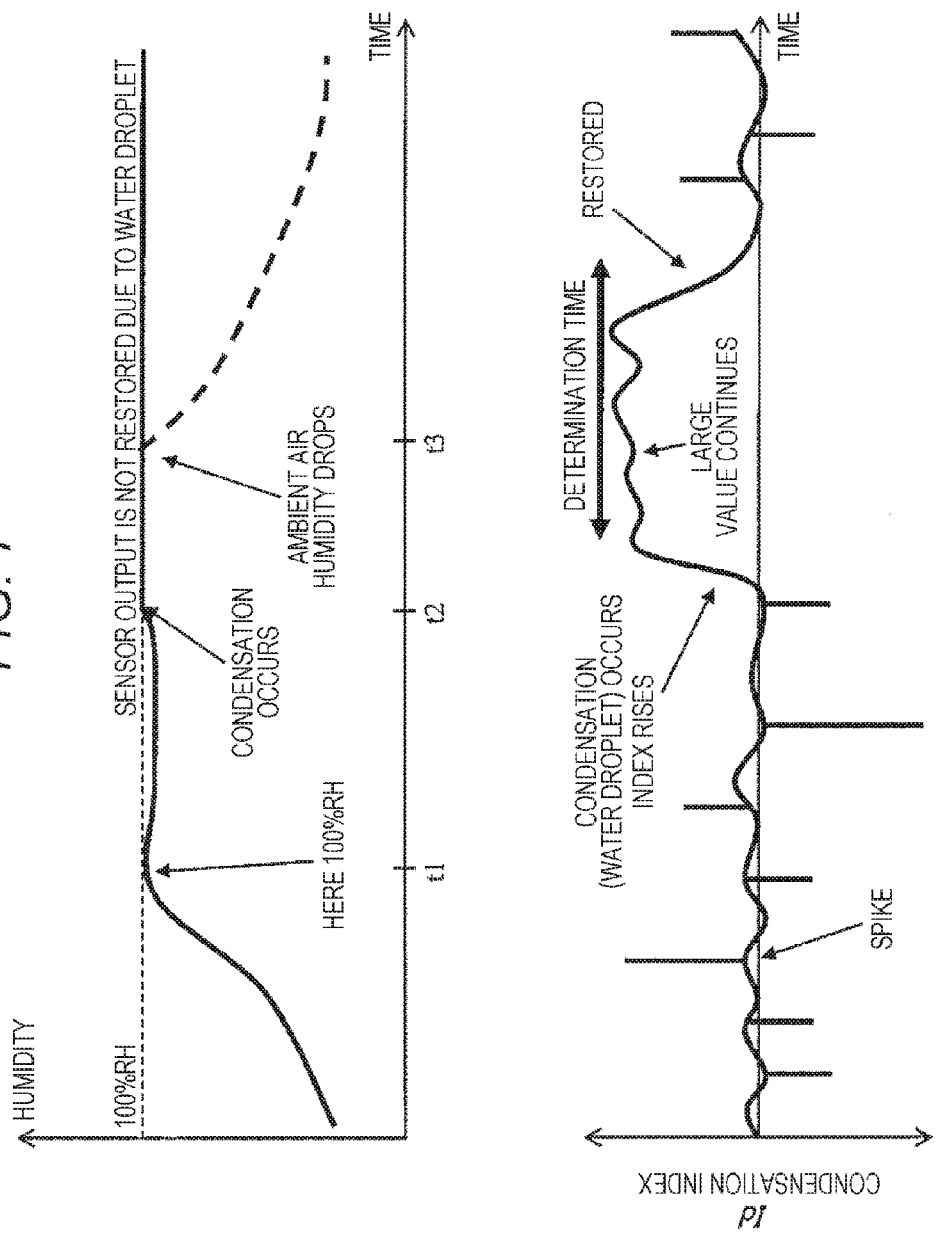
FIG. 7 is a graph showing temporal changes in humidity and a condensation determination value.
Figure 8A:
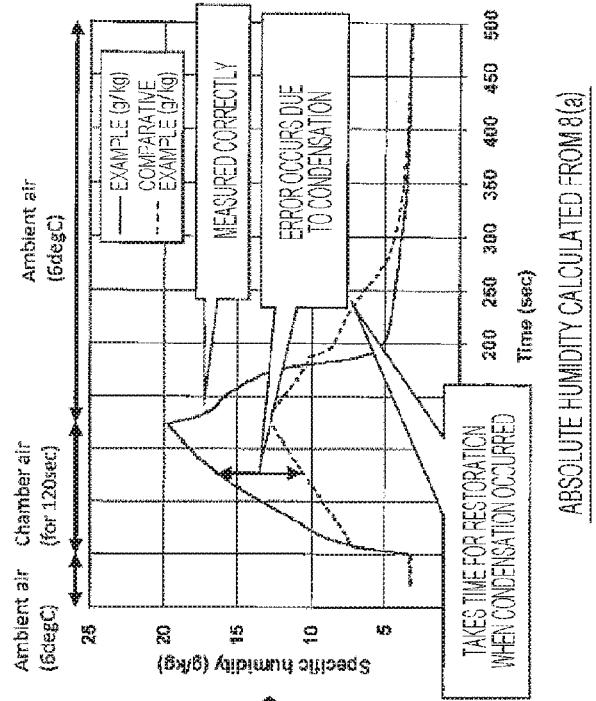
FIGS. 8A and 8B are graphs showing temperature and humidity with and without dew condensation, and absolute humidity obtained from such temperature and humidity.
Figure 8B:
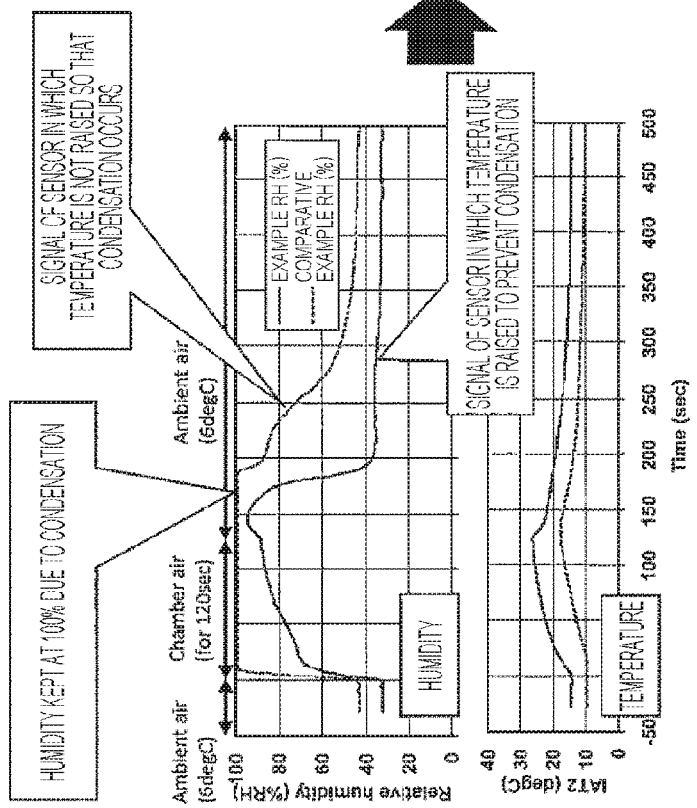

FIG. 5 is an air diagram showing a relationship among the dry-bulb temperature, the absolute humidity, and the relative humidity of the intake air. FIG. 6 is a graph showing a relationship between a change in the relative humidity and a change in the temperature. FIG. 7 is a graph showing temporal changes in the humidity and a condensation determination value. FIGS. 8(a) and 8(b) are graphs showing the temperature and the humidity with and without dew condensation, and the absolute humidity obtained from such temperature and humidity.

As shown in the air diagram of FIG. 5, the temperature and the relative humidity have a certain relationship that when the moisture content in the air is constant, a change in the temperature and a change in the relative humidity are opposite to each other, that is, when the temperature rises, the relative humidity is decreased, while when the temperature drops, the relative humidity is increased, unless a water droplet adheres to the surface of the sensor element 22.

As such, as shown in FIGS. 8(a) and 8(b) when dew condensation does not occur on the surface of the sensor element 22, accurate absolute humidity can be measured based on the relative humidity and the temperature. On the other hand, when there is dew condensation on the surface of the sensor element 22, as the relative humidity is kept at 100%, an error is also caused in the absolute humidity calculated using such relative humidity. Further, it is found that when there is dew condensation, it is impossible to promptly restore to a normal value.

The water droplet adhesion determination unit 51 determines whether or not a water droplet adheres to the surface of the sensor element 22 based on changes in the humidity and the temperature of the intake air. During operation of the engine, the temperature T of the intake air can be regarded as being always changed, and the rate of change ΔT of the temperature takes a certain value or larger. On the other hand, a detection value by the humidity sensor 21 shows relative humidity of 100% when a water droplet adheres to the surface of the sensor element 22. This brings a state where although the detection value of the temperature is changed, the detection value of the relative humidity is not changed (ΔRH≈0), whereby the relationship between the temperature and the relative humidity collapses. For example, in the example shown in FIG. 6, the actual relative humidity after dew condensation is changed while keeping a certain relationship with the temperature as shown by a broken line. However, the detection value by the humidity sensor 21 is fixed at relative humidity of 100% and is hardly changed. As such, there is no change in the humidity relative to the temperature change.

Accordingly, the index Id calculated by dividing the rate of change ΔT of the temperature by the rate of change ΔRH of the relative humidity is suddenly changed to a larger value, when a water droplet adheres to the surface of the sensor element 22. However, there is a possibility that a spike is caused with which the index Id is instantaneously increased to a larger value due to disturbance. As such, in order to determine continuity, it is determined whether or not a state where the index Id is larger than the threshold $Th_{Id}$ continues for a determination time or longer. When a state where the index Id is larger than the threshold $Th_{Id}$ continues for the determination time or longer, it is determined that a water droplet adheres to the surface of the sensor element 22.

For example, in the example shown in FIG. 7, although the relative humidity RH of the intake air takes a value around 100% at a time t1, as the index Id is in a range of not larger than the threshold $Th_{Id}$, the detection value by the humidity sensor 21 can be determined to be valid.

Then, when dew condensation occurs and a water droplet adheres to the surface of the sensor element 22 at a time t2, the detection value by the humidity sensor 21 shows relative humidity of 100%, and even when the relative humidity of the intake air drops at a time t3, the detection value by the humidity sensor 21 is kept at 100%. As such, the relationship between the temperature and the relative humidity collapses from the time t2, and the index Id is suddenly changed to a larger value. Then, when a state where the index Id is larger than the threshold $Th_{Id}$ continues for the determination time or longer, it can be determined that a water droplet adheres to the surface of the sensor element 22, whereby it can be determined that the detection value of the relative humidity by the humidity sensor 21 is invalid.

Further, when a water droplet is separated from the surface of the sensor element 22 at a time t3, for example, the detection value by the humidity sensor 21 is started to change again, and the index Id is restored to a certain reference value. As such, the detection value by the humidity sensor 21 can be determined to be valid.

In the humidity sensor 21 and the temperature sensor 31, reaction speeds and the accuracy thereof differ depending on the temperature and the humidity. As such, by changing determination conditions according to the temperature and the humidity, water droplet adhesion determination can be performed in a wide temperature range.

For example, the water droplet adhesion determination unit 51 may determine that a water droplet adheres to the surface of the sensor element 22 when the condition shown by the following Expression (2), rather than the condition of Expression (1), continues for a determination time or longer.

[Expression 2]

$$Th_{Id} < Id = \frac{\Delta T \cdot Kt}{\Delta RH \cdot Krh} \quad (2)$$

Here Kt and Krh represent fixed coefficients or coefficients determined from at least one of temperature and humidity. As described above, with use of the coefficients Kt and Krh, it is effective when the temperature and the humidity have different response speeds, for example.

Further, while description has been given on the case where the threshold $Th_{Id}$ used in Expression (1) and Expression (2) is a fixed value as an example, a function which is set based on at least one of temperature and relative humidity, as shown by the following Expression (3), is also acceptable.

[Expression 3]

$$Th_{Id}=fx(\text{temperature,humidity}) \quad (3)$$

Similarly, while description has been given on the case where the determination time is also a fixed value as an example, a function which is set based on at least one of temperature and relative humidity is also acceptable.

Further, the determination conditions may be set according to the cooling water temperature of the engine body. For example, when the cooling water temperature is low, the humidity sensor 21 is also cooled, whereby dew condensation is more likely to occur on the surface of the sensor element 22. Meanwhile, after warming up when the cooling water temperature is high, dew condensation is less likely to occur. As such, by allowing the determination conditions such as a threshold, a determination time, and coefficients to be changed according to the cooling water temperature, it is possible to perform water droplet adhesion determination in a wide temperature range.

Further, it is also possible to set conditions for performing water droplet adhesion determination. For example, during traveling of the vehicle, it is in a state where the temperature and the humidity are likely to be changed. As such, by performing water droplet adhesion determination during traveling of the vehicle, determination accuracy can be improved. Further, during operation of the engine and within a certain period of time after the operation is stopped, it is also in a state where the temperature and the humidity are likely to be changed and other disturbances are small. As such, by performing water droplet adhesion determination during operation of the engine or within a certain period of time after the operation is stopped, it is possible to improve the determination accuracy. Further, by performing water droplet adhesion determination when the cooling water temperature is low, it is possible to improve the determination accuracy.

Further, it is also possible to store the conditions having been used for water droplet adhesion determination by the water droplet adhesion determination unit 51 as past determination information, in a storage means such as the ECU 18, and when performing water droplet adhesion determination, correct the conditions to be used by comparing them with the past determination information stored in the storage means. For example, at least one of the index Id, the threshold $Th_{Id}$, and the determination time, having been used for water droplet adhesion determination by the water droplet adhesion determination unit 51, is stored as past determination information in a storage means such as the ECU 18, and when determination is performed by the water droplet adhesion determination unit 51, at least one of the index Id, the threshold $Th_{Id}$, and the determination time, to be used for present determination, is corrected by being compared with the past determination information stored in the storage means. As the probability of dew condensation differs depending on the hygroscopic property of the vehicle and the air filter, it is possible to improve the certainty of determination by storing the past index Id of the own vehicle and performing water droplet adhesion determination only when the index Id is changed largely.

Second Embodiment

Next, a second embodiment of the present invention will be described with use of the drawings.

Figure 10:
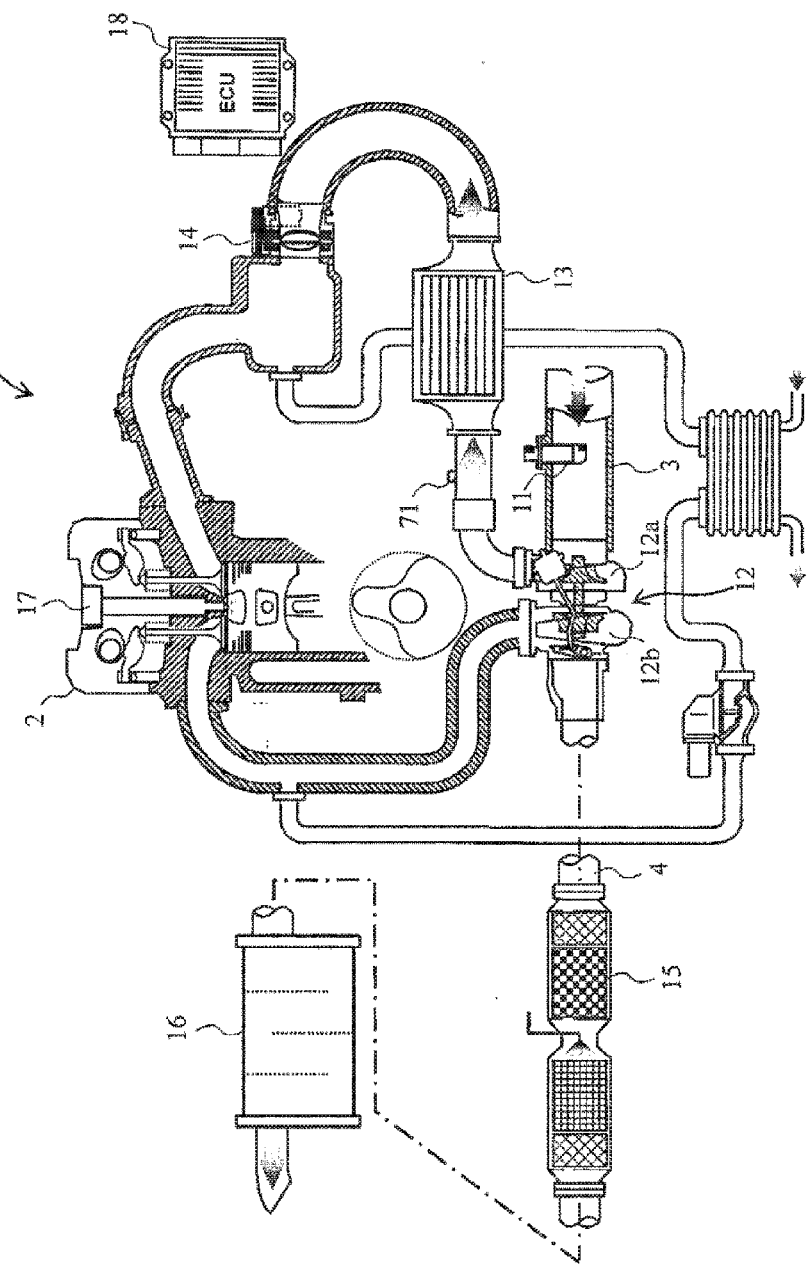
FIG. 10 is a function block diagram illustrating a second embodiment of a humidity measuring device according to the present invention.
Figure 11:
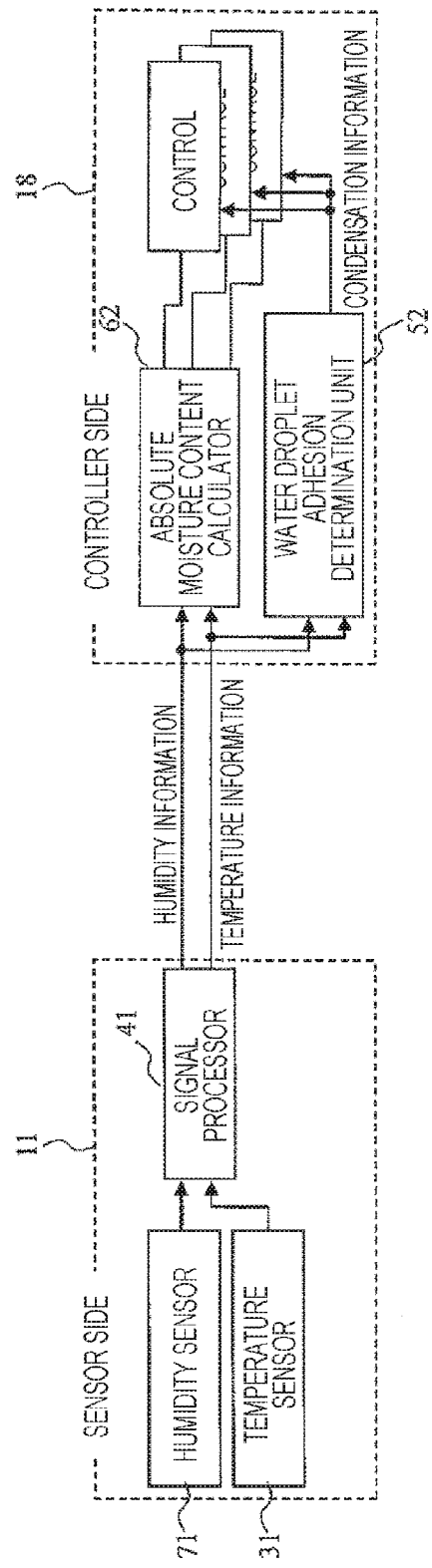
FIG. 11 is a schematic diagram of an engine control system to which the humidity measuring device of the second embodiment is applied.

FIG. 10 is a function block diagram illustrating a second embodiment of a humidity measuring device according to the present invention, and FIG. 11 is a schematic diagram of an engine control system to which the humidity measuring device of the second embodiment is applied. Similar constituent elements to those of the first embodiment are denoted by the same reference signs, and the detailed description thereof is omitted.

A feature of the present embodiment is that it is determined whether or not a detection value by a humidity sensor, which detects humidity of the intake air in which the pressure varies, is valid.

As shown in FIG. 10, a humidity sensor 71 is interposed between the compressor 12a of the turbocharger 12 and the intercooler 13 on the air intake passage 3, and detects absolute humidity of the intake air pressurized by the turbocharger 12.

As shown in FIG. 11, an absolute moisture content calculator 62 and a water droplet adhesion determination unit 52 are provided in the ECU 18, for example, and the absolute moisture content calculator 62 calculates the absolute moisture content (water vapor content) which is the moisture content in the air, based on the temperature and the absolute humidity of the intake air. Then, the water droplet adhesion determination unit 52 determines whether or not the absolute moisture content is changed to be larger than a reference value set according to the pressure of the intake air, and when it is changed to be larger than the reference value, the water droplet adhesion determination unit 52 determines that a water droplet adheres to the surface of the sensor element of the humidity sensor 71.

According to the present embodiment, it is possible to determine whether or not a water droplet adheres to the surface of the sensor element of the humidity sensor 71 which detects humidity of the intake air in which the pressure varies. Thereby, it is possible to determine whether or not a detection value by the humidity sensor 71 is valid.

While the embodiments of the present invention have been described above in detail, the present invention is not limited to those embodiments, and various changes in design can be made within a range not deviating from the spirit of the claims of the present invention. For example, the embodiments given above have been described in detail to clearly explain the present invention, and the present invention is not limited to those having the entire configurations described above. Further, a part of the configuration of an embodiment is replaceable with a part of the configuration of another embodiment, and a part of the configuration of an embodiment can be added to a part of the configuration of another embodiment. Further, with respect to a part of the configuration of each embodiment, addition of another configuration, deletion, and replacement can be made.

REFERENCE SIGNS LIST 1 engine control system
2 engine body (internal-combustion engine)
21, 71 humidity sensor
22 sensor element
31 temperature sensor
51, 52 water droplet adhesion determination unit
61 absolute humidity calculator
62 absolute moisture content calculator

The invention claimed is:

1. A humidity measuring device for measuring humidity of intake air in an internal-combustion engine, the device comprising
a water droplet adhesion determination means for determining whether or not a water droplet adheres to a surface of a sensor element which detects the humidity, based on changes in humidity and temperature of the intake air, wherein
the water droplet adhesion determination means calculates a determination value based on a rate of change of the temperature and a rate of change of relative humidity, compares the determination value with a threshold, and determines that a water droplet adheres to the surface of the sensor element when a state where the determination value is larger than the threshold continues for a determination time or longer.

2. The humidity measuring device according to claim 1, wherein
the water droplet adhesion determination means sets the threshold based on at least one of the relative humidity and the temperature of the intake air.

3. The humidity measuring device according to claim 1, wherein
the water droplet adhesion determination means sets the determination time based on at least one of the relative humidity and the temperature of the intake air.

4. The humidity measuring device according to claim 1, wherein
the water droplet adhesion determination means sets at least one of the threshold and the determination time according to a cooling water temperature of the internal-combustion engine.

5. The humidity measuring device according to claim 1, wherein
the water droplet adhesion determination means performs the determination when a cooling water temperature of the internal-combustion engine is lower than a predetermined reference water temperature.

6. The humidity measuring device according to claim 1, comprising
a storage means for storing at least one of the determination value, the threshold, and the determination time, used for the determination by the water droplet adhesion determination means, as past determination information, wherein the water droplet adhesion determination means corrects at least one of the determination value, the threshold, and the determination time, to be used for current determination, in comparison with the past determination information stored in the storage means.

7. The humidity measuring device according to claim 1, wherein
the water droplet adhesion determination means performs the determination during operation of the internal-combustion engine or within a certain period after the operation stops.

8. The humidity measuring device according to claim 1, wherein
the internal-combustion engine is mounted on a vehicle, and
the water droplet adhesion determination means performs the determination on a condition that the vehicle is traveling.

9. The humidity measuring device according to claim 1, wherein
the water droplet adhesion determination means calculates an absolute moisture content based on the temperature and absolute humidity of the intake air, and determines that a water droplet adheres to the surface of the sensor element when the absolute moisture content is changed to be larger than a predetermined reference value.

10. The humidity measuring device according to claim 9, wherein
the reference value is set according to pressure of the intake air.

* * * * *